United States Patent
Bettuzzi et al.

(10) Patent No.: US 8,044,095 B2
(45) Date of Patent: *Oct. 25, 2011

(54) MIXTURE OF CATECHINS OR RATHER POLYPHENOLS EXTRACTED FROM CHINESE GREEN TEA OR OTHER VEGETABLES FOR THE PREVENTION OF PROSTATE CANCER AND FOR THE TREATMENT OF PROSTATE HYPERTROPHY (BPH)

(75) Inventors: Saverio Bettuzzi, Montecchio Emilia (IT); Arnaldo Corti, Pontecchio (IT); Sergio Corvetta, Bolzano (IT)

(73) Assignee: Genprofiler s.r.l., Bolzano (IT)

( * ) Notice: Subject to any disclaimer, the term of this patent is extended or adjusted under 35 U.S.C. 154(b) by 579 days.

This patent is subject to a terminal disclaimer.

(21) Appl. No.: 11/658,614

(22) PCT Filed: Jul. 21, 2005

(86) PCT No.: PCT/IB2005/002107
§ 371 (c)(1),
(2), (4) Date: Jan. 16, 2008

(87) PCT Pub. No.: WO2006/013420
PCT Pub. Date: Feb. 9, 2006

(65) Prior Publication Data
US 2008/0194675 A1    Aug. 14, 2008

(30) Foreign Application Priority Data

Jul. 27, 2004 (IT) ............................. BZ2004A0037
Feb. 16, 2005 (IT) ............................. BZ2005A0004

(51) Int. Cl.
*A61K 31/35* (2006.01)
(52) U.S. Cl. ....................................................... 514/456
(58) Field of Classification Search .................. 514/456
See application file for complete search history.

(56) References Cited

U.S. PATENT DOCUMENTS

| | | | |
|---|---|---|---|
| 6,410,052 B1 * | 6/2002 | Morre et al. | 424/729 |
| 6,410,061 B1 * | 6/2002 | Morre et al. | 424/729 |
| 6,652,890 B2 * | 11/2003 | Morre et al. | 424/729 |
| 6,759,064 B2 * | 7/2004 | Morre et al. | 424/729 |
| 2003/0105030 A1 | 6/2003 | Liao et al. | 514/27 |

FOREIGN PATENT DOCUMENTS

| WO | WO00/33832 | 6/2000 |
|---|---|---|
| WO | 02/067965 | 9/2002 |

OTHER PUBLICATIONS

Montironi et al. Adv. Clin. Path., 1997, vol. 1, No. 1, pp. 35-47 (Abstract Attached).*
Adhami et al. J. Nutr., 2003, vol. 133, pp. 2417S-2424S.*
Ahn et al, EPO Jour of Cancer Prev, vol. 12, No. 5, 2003, pp. 383 390, Protective effects of green tea extracts (polyphenon E . . . ).
Ullmann et al, Jour of Intl Med Res 31, 2003, pp. 88-101, A Single Ascending Dose Study of Epigallocatechin Gallate in . . . .
Gupta et al, PNAS, vol. 98, No. 18, Aug. 28, 2001, pp. 10350-10355, Inhibition of prostate carcinogenesis in TRAMP mice by oral . . . .
Crowell, Abstracts of Papers Amer Chem Soc, vol. 226, No. 1-2, 2003, p. AGFD 64, Preclinical and Clinical Development . . . .
Hastak et al, Oncogene 22, 2003, pp. 4851-4859, Role of p53 and NF-$_\kappa$B in epigallocatechin-3-gallate-induced apoptosis of . . . .
Zhu et al, Xenobiotica, vol. 31, No. 1, Jan. 2001, pp. 51-60, Pharmacokinetics and system linearity of tea catechins in rat.
Bettuzzi et al, European Urology Supp, vol. 3, No, Feb. 2004, p. 91, The chemopreventive action of catechins in the TRAMP mice . . . .
Saleem et al, Nutrition and Cancer, vol. 47, No. 1, 2003, pp. 13-23, Tea beverage in chemoprevention of prostrate cancer.

* cited by examiner

*Primary Examiner* — James Anderson
(74) *Attorney, Agent, or Firm* — Fish & Associates, PC

(57) ABSTRACT

The formulation and modality of use of a pharmaceutical preparation having the properties described below is described. This preparation is a product comprising a mixture of catechins or polyphenols extracted from chinese green tea or other vegetables that has proven to be efficacious in the chemical prevention of prostate cancer in a clinical pilot study when administered in adequate systemic dosage without the aid of other conventional drugs or remedies and without adverse effects in a group of subjects at risk of development of the illness. The same reduction of the preparation proved efficacious in symptomatology of benign prostate hypertrophy and especially as concerns the difficulty of urination when administered in adequate dosage systemically without the aid of other drugs or conventional remedies and without adverse effects in the patients subject of the study.

10 Claims, No Drawings

MIXTURE OF CATECHINS OR RATHER POLYPHENOLS EXTRACTED FROM CHINESE GREEN TEA OR OTHER VEGETABLES FOR THE PREVENTION OF PROSTATE CANCER AND FOR THE TREATMENT OF PROSTATE HYPERTROPHY (BPH)

This is a national stage of PCT/IB05/002107 filed Jul. 21, 2005 and published in English.

The medicinal properties of Chinese green tea (*Camellia sinensis*) have been known since antiquity. Based on present-day medical knowledge, tea possesses numerous beneficial properties among which are stimulating, digestive, diuretic, analgesic and detoxifying properties. The beneficial effects on health attributed to green tea are due to the fact that, differently from black tea or other types of tea, it is prepared in accordance with a procedure capable of avoiding fermentation processes and allowing better conservation of numerous substances and active principles in the leaves and among these a good part of the positive effects of green tea for the health of man is attributed particularly to the catechins, polyphenolic compounds having powerful antioxidant action and capable of eliminating free radicals.

Catechins are a family of compounds to which belong different molecules. Indeed, the polyphenol content of green tea represents approximately 30% of dry weight and consists of flavanols, flavandiols, flavonoids and phenolic acids. Chinese green tea is therefore an excellent primary source for purification in large quantities of catechins but it is known that these molecules are also extractable from other plants that supply smaller quantities thereof but the material obtained shows the same properties as that obtained from Chinese tea. In any case, the flavanols represent the greater part of the polyphenols of green tea and are commonly known by the name catechins. The most important catechins of green tea are the following:
(−)-epigallocatechina-3-gallato (EGCG),
(−)-epigallocatechina (EGC),
(−)-epicatechina-3-gallato (ECG),
(+)-gallocatechina-3-gallato (GCG),
(−)-epicatechina (EC),
(+)-gallocatechina (GC),
(+)-catechina (C).

Alkaloids like caffeine, theobromine and theophylline represent approximately 4% of the dry weight of tea leaves and in the preparation described by us below they are removed to prevent their administration and possible undesired effects (see below). Typically, a cup of green tea (200 ml) contains 80-90 g of catechins of which EGCG is more than 50% (1). The flavanols are easily oxidized and make up the corresponding 0-quinones. Flavonols and quinones can function either as accepters or as donors of hydrogen. In addition, the polyphenols of tea react efficiently with the reactive species of oxygen. In the structure of the flavonols the hydroxylic groups in position 5-7 and oxygen in position 1 make the carbon atoms in positions 6 and 8 highly nucleophilic during enzymatic and non-enzymatic oxidation. The tea flavonols can go towards oxidizing condensation through the formation of C—O links or C—C in oxidizing polymerization reactions. There are three mechanisms through which the polyphenols exercise their antioxidant effects, to wit:

a) the presence of the 'catechol' structure confers a strong calming power on the tea catechins, that can link the free ferric and ferrous ions, which are necessary for formation of the reactive radicals of oxygen, and lower their cellular concentration, b) EGCG, EGC and ECG carry out a very effective action in the elimination of superoxide and hydroxide anionic radicals, two of the more reactive species of oxygen that can damage the DNA and other molecules of the cell and can start lipidic peroxidation, and c) tea flavanols can react with the peroxylic radicals and this way put an end to the chain reactions of lipidic peroxidation. The reactive species of oxygen can fulfill an important role in carcinogenesis through DNA damage, alteration of the genic expression or influencing growth and cellular differentiation.

Recent studies have shown that the polyphenolic compounds administered in the form of green tea infusion or powder are absorbed rapidly at the gastric level and distributed in the protein fraction of the plasma and in the fraction containing the high-density lipoproteins (HDL). The catechin content of the plasma increases proportionately to the amount taken. The half-life of EGCG in plasma is slightly over 5 hours. Different metabolites of the catechins have been identified in plasma and urine in the form of methylate compounds or conjugated with glucuronic acid or sulphates. Considering that it has been shown that the antioxidant power in plasma continues for a period of time longer than the average life of the polyphenols ingested, it is believed that the metabolites of the catechins possess properties beneficial for man. In any case, administration every 6 hours of the formulation described ensures a constant contribution of the active principles and in particular of EGCG, which appears to be the component of greatest activity.

The above-mentioned capability to act as powerful antioxidants has the result that the polyphenols and especially the EGCG act as powerful anti-stress and anti-aging factors, conditions that both play a causative role in a pathology like prostate cancer that is clearly correlatable with man's aging. In addition, it must be underscored that EGCG and the other catechins revealed themselves in different experimental models to be capable of inhibiting the effects of testosterone. It is known that androgenic action is also involved in the genesis of the prostate pathologies and in particular of prostate cancer. This constitutes the scientific rational that proves how the systemic administration of a formulation capable of contributing an adequate dose of EGCG and catechins can be effective in the chemical prevention of prostate cancer in patients at risk.

Additional elements derive from numerous in vitro studies that have shown a possible antiproliferation and antitumor role of these compounds. These same studies on laboratory animals and on man have again shown the absence of toxicity or other collateral effects of the catechins administered up to 1 g per day.

These molecules having such interesting properties are not typical only of Chinese green tea but are also present in numerous other kinds of vegetables such as the grapevine and vegetable produce typical of the Mediterranean environment. It is thus clear that any product making use of a mixture of these compounds or of some purified molecules even from other sources that are not Chinese green tea fall under this intellectual patent.

Experimental Evidence of the Effectiveness of EGCG and of a Mixture of CATECHINS (Polyphenols) for the Chemical Prevention of the Onset of Prostate Cancer Evidence of the chemically preventive effectiveness of EGCG and catechins was proven by ourselves in vitro and in preclinical animal models.

A study performed in normal human prostate epithelial cells (EPIT) in a line of human prostate epithelial cells immortalized by means of stable expression of the antigens SV40 (PNT1a) and in prostate cancer cells isolated from bone metastases (PC-3) showed selective action dependent on PNT1a and PC-3 of EGCG. A dose-response study performed by administering increasing quantities of EGCG to the above-mentioned cells in culture showed that, while the growth of EPIT was not modified significantly after that treatment, the $IC_{50}$ of EGCG in PNT1a was very lower than in PC-3, showing that especially the immortalized cells (less obviously the tumorigenics also) entered in a proliferative block and were sent to cellular death by apoptosis. This suggests that EGCG and catechins are particularly effective in inhibiting the initial phases of the neoplastic transformation.

To show the validity of this hypothesis we worked on a preclinical animal model of dogs or prostate. One of the more important preclinical models for the study of prostate tumor in vivo consists of transgenic rats TRAMP. These animals, when recombinant homozygotes develop prostate cancer with 100% probability in the adult stage. Progress of the illness recapitulates the essential phases of onset and progress of the human ailment. Indeed, it begins with lesions of the Prostate Intraepithelial Neoplasia (PIN) type to then give full blown neoplastic histological lesions, evolve subsequently towards androgen-resistant and aggressive phenotypes, then originating extraprostate and metastatic lesions in the terminal phase. We showed in our laboratories that the administration of a formulation of catechins extracted from green tea similar to the characteristic one indicated below in drinking water proved very effective in the chemical prevention of prostate cancer in rats TRAMP. Reduction of the onset of this neoplasia in treated animals was 80% (only 20 cases of neoplasia in 100 against 100 out of 100 in untreated animals). In addition, the animals in which chemical prevention proved ineffective showed in any case the presence of tumoral lesions confined to the prostate without metastatic lesions.

The results we obtained in vitro and in the animal model in which we did not witness any adverse or collateral effect suggest that taking the catechins might cause blocking of the tumoral process and hence act favorably on any progression of the illness in vivo. This prerequisite is the rational for attempting a chemical prevention of prostate cancer in man.

We therefore planned and carried out a study to verify this hypothesis. For this purpose, a population of subjects with high risk of developing the neoplastic illness (subjects in which the high-degree pre-neoplastic lesion PIN was shown by means of prostate needle-biopsy) was subjected to treatment with the formulation indicated below with doses of 600 mg per day Vs placebo (divided in 3 administrations per day) for a total duration of 1 year with double-blind randomization procedure.

After the initial test of high-degree PIN, the subjects were convened every 3 months to receive 9 boxes of capsules at a time, a quantity sufficient for a 3-month treatment. Each subject was already included previously in a 'watchful waiting' program performed at the afferent urology department. Every 3 months each subject was recalled to perform the case-history, objective examination, total and free PSA. At 6 and 12 months from the beginning of the study, case-history, objective examination, trans-rectal echography and prostate mapping were performed by the urology department. The number of biopsy samples was between 8 and 18. During the observation period an initial prostate needle-biopsy was performed to show the high-degree PIN, one at 6 months and one at 1 year excepting cases in which sudden rise in the PSA, alteration of other clinical parameters or the onset of characteristic symptomatologies reported by the subjects during the objective examination had suggested the reasonable necessity of performing the examination earlier.

In case of diagnosis of adenocarcinoma, the patient dropped out of the study immediately (failure of the chemical prevention) and was sent to the recommended therapy suggested by the reference urologist.

The subjects were followed for the duration of at least 1 year and during the study the following were assessed, at 6 and 12 months:
number of cases of onset of carcinoma of the prostate in the two branches of the study (treated against placebo),
average time of onset of carcinoma compared with the date of diagnosis of PIN,
objective symptomatology,
Gleason degree,
clinical stage,
variations of the PSA figures,
prostate volume.

At each check during the objective examination the doctor took note of the possible collateral or undesired effects arising during the treatment with catechins.

Results: in the branch of the subjects treated, no case of onset of prostate cancer was verified neither after 6 months nor after 1 year from the beginning of treatment whereas in the branch treated with placebo the onset was respectively 30% and 40% which is very close to the expected results. Indeed, from an examination of the scientific literature on the subject it is inferred that the risk of onset of prostate cancer in subjects with high degree PIN is 50% within 1 year.

To sum up, the formulation described below proved to be extremely effective in preventing the onset of prostate cancer after 6 months and 1 year of treatment in patients with high risk of onset (high degree PIN).

It is very important to underline that the systemic administration of the above-mentioned doses of the formulation which is the subject of this patent did not show any risk for patients nor any collateral or adverse effect during the entire time of treatment and therefore the effects described are associated with the absence of risk of toxicity or any other collateral effect. The treatment was particularly well accepted by the subjects; the latter reported a diffused state of well-being and more vigor.

Effects and Therapeutical Properties of the Product in Benign Prostate Hypertrophy (BPH)

The capability mentioned in the Introduction of acting as a very powerful antioxidant and anti-stress and anti-aging factors suggests a beneficial action thereof on prostate hypertrophy symptomatology. Indeed, it is known that such conditions play a causal role in prostate hypertrophy, an illness that is clearly correlatable with man's aging. In addition, it is underscored that these compounds proved capable in different experimental models of inhibiting the effects of testosterone. The androgenic action is also involved in the genesis of prostate pathology and hypertrophy. This constitutes the scientific rational that proves how the systemic administration of a formulation capable of contributing an adequate dose of catechins can be effective in the prevention and reduction of the symptomatology correlated with benign prostate hypertrophy. It is also very important to underscore that systemic administration of the doses indicated below of the formulation which is the object of this invention did not reveal any risk for the patients during all the time of treatment and therefore the effects described are associated with the absence of risk of toxicity or any other collateral effect.

The experiments conducted by ourselves on an adequate number of clinical cases showed that the daily administration of three capsules containing the above-mentioned formulation without the aid of other remedies or drugs proved efficacious after 3 months of treatment by strongly reducing the prostate symptomatology and in particular in improving urination (duration, time of waiting, emptying of the bladder) and reducing nocturnal urination while allowing uninterrupted sleep and consequently bringing a considerable improvement to the quality of the patient's life. The beneficial effects recorded proved comparable or often better than those obtainable with the use of therapeutical remedies known and conventionally used like alpha-lithics, phytosanitary products and anti-androgenics (phinasterids).

DESCRIPTION OF THE PRODUCT

The product administered to the voluntary human subjects appears as capsules or tablets containing 200 mg each of the following mixture of polyphenols (catechins) extracted from green tea coming from the best locations of China or from other vegetable sources as described above and made up as follows.

| | |
|---|---|
| Total catechins (EC, ECG, EGC, GCG, EGCG): | not less than 80 |
| of which EGCG: | not less than 50 |
| Caffeine: | less than 1.5 |
| Gallic acid, other catechins and derivatives of the oxidation of catechins: | less than 20 |

As may be seen, the extract was decaffeinated to bring the caffeine content down to a very low level (less than 1.5%) corresponding to a figure lower than that contained on average in a half cup of tea. This treatment allows use of the preparation without causing states of excitation and without interfering with sleep in case of systemic administration in the evening. The recommended dosage is 3 capsules per day for the first 3 months, which corresponds to the polyphenol content in 5 to 10 cups of green tea, possibly taken with the main meals. This dosage allows for the fact that in oriental countries (where the incidence of prostate pathologies, BPH and prostate cancer is much lower that in the west) typical consumption is 10 cups of green tea per day. In addition, it has been reported in the scientific literature that administration of 1 g per day of catechins to male and female volunteers between 21 and 71 years of age had no harmful effect.

These molecules with such interesting properties are not typical only of Chinese green tea but are also present in numerous other kinds of vegetables, meat and products of the vine and vegetable products typical of the Mediterranean environment. It is thus clear that any product making use of a mixture of these compounds or of one or several purified molecules even from sources other than Chinese green tea falls within the scope of protection of this invention.

Effects and Therapeutical Properties of the Product Learned Objectively.

The experiments made by us on an adequate number of clinical cases showed that daily administration of three capsules containing the above-mentioned formulation without the aid of other remedies or drugs proved to be effective after 6 months and 1 year of treatment in reducing to zero the onset of prostate cancer in patients at risk (high degree of PIN).

In order to prevent the onset of prostate cancer in man and obtain benefit in the symptoms of benign prostate hypertrophy, on the basis of the foregoing, the intellectual property right of the above-mentioned formula and of all the possible associations and variations in different proportions of the components and active vegetable properties and especially of catechins is claimed as we found that the production of an analogous product obtained with different proportions of catechins or with purified EGCG or other individual purified catechins still preserves beneficial properties even if our experiments would seem to show that the association and proportions used by ourselves offer greater advantages in terms of effectiveness, absorption and metabolism, product storability and reproducibility of results. In addition, even the use of other kinds of vegetables among which those mentioned above as primary sources for the purification of catechins falls under this patent as it is known that the active principles that determine the beneficial properties of the product described are the catechins (polyphenols) and n particular EGCG and that these molecules are extractable—even though in different quantities and with different efficiency—even from other vegetables strictly correlated with *Camellia sinensis* in taxonomic terms and from still others like the grapevine and its products and numerous vegetables typical of Mediterranean type nutrition.

Use of said preparation for the above-described therapeutic purposes is claimed. In particular, use of the formulation for the production of medicines and over-the-counter products or naturalistic or homeopathic medicines whatever be the vehicle or the excipients added to the formulation or the way of administration or the dosage and the different procedures of use or preservation for the treatment of benign prostate hypertrophy (BPH) and its symptomatology and for prevention of the onset of prostate cancer in man for chemically preventive and therapeutical purposes is therefore claimed.

Since thanks to the completeness of our studies which range from the cellular models in vitro to pre-clinical animal models right up to man, we identified the efficacious active principles in the chemical prevention of human prostate cancer, and for treatment of benign prostate hypertrophy symptoms, they fall under this claim independently of the purification procedure adopted because it is their use that shows the beneficial properties. The intellectual property right of analogous syntheses showing the same beneficial properties in man is therefore claimed.

The invention claimed is:
1. A method of preventing onset of prostate cancer for at least six months in a person diagnosed with preneoplastic lesion prostatic intraepithelial neoplasia (PIN), comprising the steps of:
   (a) diagnosing a disease stage of the prostate in the person;
   (b) exclusively upon diagnosis of preneoplastic lesion PIN providing for oral administration a mixture of compounds that includes at least 80% total catechins with at least 50% of the total catechins being epigallocatechin gallate (EGCG), and with less than 20% of the mixture being gallic acid; and wherein
   (c) the composition is administered to the person having preneoplastic lesion PIN using a schedule and at a concentration effective to prevent onset of prostate cancer in the person over a period of at least six months.

2. The method of claim 1 wherein the compounds are isolated from green tea.

3. The method of claim 1 wherein the compounds are identical with compounds isolated from green tea.

4. The method of claim 1 wherein the mixture is formulated in a capsule for oral administration.

5. The method of claim 4 wherein the capsule includes 200 mg of the mixture.

6. The method of claim 5 wherein the schedule includes daily administration of three doses.

7. The method of claim 6 wherein administration of the capsule is maintained over at least 6 months.

8. The method of claim 6 wherein administration of the capsule is maintained over at least 12 months.

9. A method of preventing onset of prostate cancer for at least six months in a person diagnosed with preneoplastic lesion prostatic intraepithelial neoplasia (PIN), comprising the steps of
   (a) diagnosing a disease stage of the prostate in the person;
   (b) exclusively upon diagnosis of preneoplastic lesion PIN providing for oral administration an orally administered composition that includes at least 480 mg of total catechins with at least 300 mg of the total catechins being epigallocatechin gallate (EGCG), and with less than 120 mg of the composition being gallic acid; and
   (c) wherein the composition is administered to the person having preneoplastic lesion PIN using a schedule and at a concentration effective to prevent onset of prostate cancer in the person diagnosed with preneoplastic lesion PIN over a period of at least six months.

10. The method of claim 9 wherein the schedule comprises three times daily oral administration.

* * * * *